US012303305B1

(12) United States Patent
Cao et al.

(10) Patent No.: US 12,303,305 B1
(45) Date of Patent: May 20, 2025

(54) MONITORING AND EARLY WARNING DEVICE FOR PREVENTING FALLING DURING GETTING UP OF OLD PEOPLE

(71) Applicant: Hangzhou Normal University, Hangzhou (CN)

(72) Inventors: Shihua Cao, Hangzhou (CN); Wenhao Qi, Hangzhou (CN); Bin Wang, Hangzhou (CN); Shiying Shen, Hangzhou (CN); Chaoqun Dong, Hangzhou (CN); Xiaohong Zhu, Hangzhou (CN); Sixie Li, Hangzhou (CN); Jianwen Zeng, Hangzhou (CN); Xin Liu, Hangzhou (CN); Jiani Yao, Hangzhou (CN); Xiajing Lou, Hangzhou (CN); Yankai Shi, Hangzhou (CN); Bingsheng Wang, Hangzhou (CN); Han Shi, Hangzhou (CN)

(73) Assignee: HANGZHOU NORMAL UNIVERSITY, Hangzhou (CN)

( * ) Notice: Subject to any disclaimer, the term of this patent is extended or adjusted under 35 U.S.C. 154(b) by 0 days.

(21) Appl. No.: 18/970,950

(22) Filed: Dec. 6, 2024

(30) Foreign Application Priority Data

Jul. 31, 2024 (CN) .......................... 202411038286.2

(51) Int. Cl.
*A61B 5/00* (2006.01)
*A61B 5/11* (2006.01)
*A61G 7/05* (2006.01)
*A61G 7/10* (2006.01)
*G08B 21/04* (2006.01)

(52) U.S. Cl.
CPC ............ *A61B 5/746* (2013.01); *A61B 5/1117* (2013.01); *A61B 5/7405* (2013.01); *A61G 7/0506* (2013.01); *A61G 7/0525* (2013.01); *A61G 7/1073* (2013.01); *G08B 21/043* (2013.01); *A61G 2203/30* (2013.01); *A61G 2203/34* (2013.01)

(58) Field of Classification Search
CPC .............. A61G 7/1073; A61G 2203/30; A61G 2203/34; G08B 21/043
See application file for complete search history.

(56) References Cited

FOREIGN PATENT DOCUMENTS

| CN | 115569010 A | 1/2023 |
|---|---|---|
| CN | 115645167 A | 1/2023 |

*Primary Examiner* — Brian A Zimmerman
*Assistant Examiner* — Cal J Eustaquio

(57) ABSTRACT

A monitoring and early warning device for preventing falling during getting up of old people is provided by the disclosure, relating to safety protection for the old people. The device includes a bedstead mechanism, a lifting auxiliary mechanism is arranged at the top of the bedstead mechanism. When the motion sensor monitors an instantaneous acceleration behavior, it's judged that the old people fall; when the TOF radar detects a long-term static behavior of the old people in the external area of the device, it's judged that the old people drop. Abnormal behavior activates the acousto-optic alarm and sends early warnings to intelligent terminals of accompanying personnel and medical staff through a built-in module for warning. Staff unable to offer immediate help could turn on the camera to watch the image information near the device through the intelligent terminal at this time, and take actions based on the old people's condition.

5 Claims, 8 Drawing Sheets

US 12,303,305 B1

MONITORING AND EARLY WARNING DEVICE FOR PREVENTING FALLING DURING GETTING UP OF OLD PEOPLE

TECHNICAL FIELD

The disclosure relates to the technical field of safety protection for the old people, and in particular to a monitoring and early warning device for preventing falling during getting up of old people.

BACKGROUND

With the continuous development of science and economy, as well as the ongoing progress of society, the average human lifespan has been universally extended. The phenomenon of elderly individuals living to advanced ages has become widespread. Due to the aging process, individuals experience physiological degenerative changes, a decline in psychological cognitive functions, and a reduction in social adaptability, which collectively introduce numerous safety hazards for the old people during their activities.

At present, patients suffering from hospitalization have reduced balance ability due to decreased body functions, and accidents such as bed falling and falling may occur slightly when leaving the hospital bed.

Therefore, a monitoring and early warning device for preventing falling during getting up of old people is provided, so as to solve the problems proposed in the background.

SUMMARY

The present disclosure provides a monitoring and early warning device for preventing falling during getting up of old people, so as to solve the problems proposed in the background.

In order to achieve the above purpose, the disclosure provides a following technical scheme: a monitoring and early warning device for preventing falling during getting up of old people includes a bedstead mechanism, where a lifting auxiliary mechanism is arranged at the top of the bedstead mechanism, testing mechanisms are symmetrically arranged at positions close to two sides at the top of the bedstead mechanism, a headrest mechanism is arranged at the back side of the bedstead mechanism, and a detection mechanism is arranged at the position close to the front side at the top of the bedstead mechanism. The lifting auxiliary mechanism includes a fixed frame, a first rotating frame and a second rotating frame, where tops of the fixed frame, the first rotating frame and the second rotating frame are all connected to a plurality of lap plates; a mattress is arranged between the tops of the plurality of lap plates; first pressure sensors are embedded in the top of the mattress; the two testing mechanisms both include side baffles; air bags are installed on the outer surfaces of the opposite sides of the two side baffles, a plurality of second pressure sensors are embedded in the outer surfaces of the opposite sides of the two air bags in an array mode, and optical fiber refractive index sensor groups are symmetrically installed at the positions, close to the inner side, of the tops of the two side baffles.

Optionally, the bedstead mechanism includes an underframe, where the top of the underframe is fixedly connected to support columns at positions close to four corners; a support frame is fixedly connected between the tops of the plurality of support columns; the fixed frame is fixedly connected to the top of the support frame at positions close to the front side; the bottoms of the first rotating frame and the second rotating frame are attached with the top of the support frame; two first rotating seats are fixedly connected to a position, close to the rear side, of the top of the underframe, and universal wheels are mounted at positions, close to the four corners, of the bottom of the underframe.

Optionally, the outer surface of the support frame is provided with side openings at positions close to both sides, and a first rotating shaft is rotatably connected between the front and rear inner surface walls of the side openings, the side baffles are located between the inner surface walls of the side openings, the outer surface of the first rotating shaft is connected to the inner surface walls of the side baffles. The front surface of the support frame is provided with first motors at positions close to both sides, and output ends of the first motors rotate through the front surface of the support frame and is fixedly connected to the front end of the first rotating shaft.

Optionally, the top of the side baffle is provided with a first sliding groove near the outside, a first screw rod is rotatably connected between the front and rear inner surface walls of the first sliding groove, a first sliding block is slidably embedded between the inner surface walls of the first sliding groove, and the outer surface of the first screw rod is threaded through the outer surface of the first sliding block.

Optionally, a second motor is installed on the front surface of the side baffle, the output end of the second motor rotates through the front surface of the side baffle and extends to the other side, the output end of the second motor is fixedly connected to the front end of the first screw rod, and a range finder is installed on the top of the first sliding block.

Optionally, the detection mechanism includes a long rod, the long rod is fixedly installed at the top of the support frame near the front side, the top of the long rod is fixedly connected to a mounting rod; a camera is arranged at the bottom of the mounting rod near the rear edge; a motion sensor is arranged at the front side of the camera at the bottom of the mounting rod; a TOF radar is arranged at the front side of the motion sensor at the bottom of the mounting rod; and an acousto-optic alarm is arranged at the top of the mounting rod.

Optionally, rotating heads are installed on the front surfaces of the first rotating frame and the second rotating frame, where one rotating head is rotatably connected to the rear surface of the fixed frame, and the other rotating head is rotatably connected to the rear surface of the first rotating frame, and connecting rods are fixedly connected between the inner surface walls on both sides of the first rotating frame and the second rotating frame.

Optionally, the outer surface of the connecting rod is rotatably connected to a first rotating sleeve, the bottom of the first rotating sleeve is connected to a first electric push rod, the bottom of the first electric push rod is connected to a second rotating sleeve, and the two second rotating sleeves are respectively rotatably connected to the two first rotating seats, and the outer surface of the mattress is provided with a strap, and the outer surface of the strap passes through the bottom of the adjacent lap plates.

Optionally, the headrest mechanism includes a headstock, the front surface of the headstock near the bottom is fixedly connected to the rear surface of the support frame, the front surface of the headstock is slidably connected to a mounting plate, the front surface of the headstock near the middle is provided with a second sliding groove, a second screw rod is rotatably connected between the inner top and the inner bottom of the second sliding groove, and a second sliding block is fixedly connected to the rear surface of the mounting plate near the middle. The outer surface of the second screw rod is threaded through the outer surface of the second sliding block, the top center of the headstock is rotatably connected to a first pulley, the bottom of the first pulley is fixedly connected to the top of the second screw rod through a shaft, a third motor is fixedly installed on the rear surface of the headstock, the output end of the third motor is fixedly connected to a second pulley, and a transmission belt is connected between the second pulley and the outer surface of the first pulley in a transmission way.

Optionally, the front surface of the headstock is symmetrically provided with avoidance grooves at positions on both sides of the second sliding groove, second electric push rods 510 are symmetrically mounted on the rear surface of the mounting plate 503, the telescopic ends of the second electric push rods slide through the rear surface of the mounting plate and extend to the front side, the second electric push rods are located between the inner surface walls of the avoidance grooves, the front ends of the two second electric push rods are fixedly connected to second rotating seats, and rotating blocks are rotatably connected between the inner surface walls of the second rotating seats. A headrest backrest is fixedly connected between the front surfaces of the two rotating blocks, and a connecting frame is fixedly connected between the outer surfaces of the two second rotating seats; a biaxial motor is installed on the front surface of the connecting frame, and the output ends at both sides of the biaxial motor respectively penetrate the outer surfaces of the two second rotating seats and are connected to the two rotating blocks.

Compared with the prior art, the disclosure has following beneficial effects.

First, when the device is used, the optical fiber refractive index sensor groups on the two sides form a detection horizontal line and are matched with the first pressure sensors in matrix form in the mattress and the second pressure sensors in matrix form in the air bags on the two sides, so that the sleeping posture and the sitting posture of the old people can be monitored; when the old people get up at night, the range finder plays a role in judging the direction of getting out of bed, and then the first motors and the first rotating shaft are matched to turn down the corresponding side baffle and related components, which is convenient for the old people to get out of bed; during the process, the motion sensor continuously monitors the motion speed of the old people, and the TOF radar monitors the external area of the device. When the motion sensor monitors a instantaneous acceleration behavior, it is judged that the old people fall, and when the TOF radar detects a long-term static behavior of the old people in the external area of the device, it is judged that the old people drop. Abnormal behavior activates the acousto-optic alarm and sends early warnings to the intelligent terminals of accompanying personnel and medical staff through a built-in module for warning. Staff unable to offer immediate help could turn on the camera to watch the image information near the device through the intelligent terminal at this time, and take actions based on the old people's condition. The disclosure has high overall intelligence, can effectively avoid falling accidents caused by the old people getting up alone, and has a good guarding effect.

Second, when the disclosure is used, when the first pressure sensors and the second pressure sensors detect the action of the old people getting up, the first pressure sensors judge the supporting position of the upper body of the old people according to the pressure weakened area, extends and pushes the connecting rod to move upwards at the same time according to the first electric push rod at the position corresponding to the position of the old people body, at the moment, the corresponding first rotating frame and the corresponding second rotating frame reversely rotate upwards, so that the upper body of the old people is pushed to form assistance force, the corresponding part of the mattress can be lifted, meanwhile, the lifted first pressure sensors can feed back to the first electric push rod according to the pressure value to achieve the effect of controlling the pushing speed, the effect of independently taking the bed by old people is facilitated under mutual cooperation, the intelligent degree is high, and the use of old people is facilitated.

Third, during use, the third motor can be started to drive the second pulley to rotate according to the sleep or sitting state of the old people, the first pulley can be synchronously driven to rotate through cooperation of the transmission belt, the second screw rod in the second sliding groove can be driven to rotate in the rotating process of the first pulley and drive the second sliding block to ascend and descend, in the lifting process of the second sliding block, the headrest backrest can be driven to be adjusted to a low position through the mounting plate and other mechanisms to be used as a backrest after being used or adjusted to a high position, the headrest backrest can be adjusted to a medium height in the getting-up process of old people, and then after the second electric push rod is started, the headrest backrest is pushed to be attached to the back of the old people and slowly pushed forwards to form power assistance, in the process, the biaxial motor drives the rotating blocks in the two second rotating seats to overturn up and down and then adjust the backrest angle of the headrest, so that the headrest backrest is always attached to the back of the old people, the comfort degree in the pushing process is improved, the sitting effect of the old people is assisted, and the practicability of the device is improved.

Figure 1:
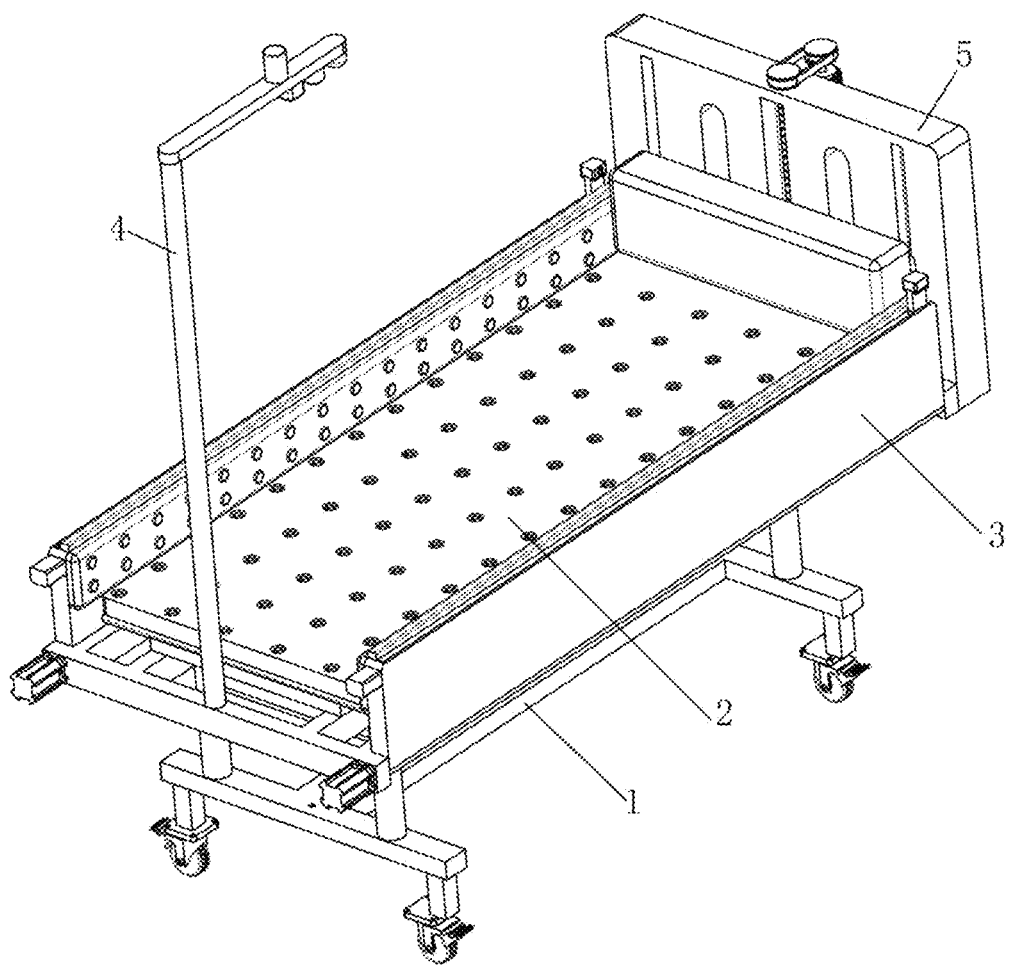
FIG. 1 is a perspective view of a monitoring and early warning device for preventing falling during getting up of old people.

In the figures: 1. bedstead mechanism; 101. underframe; 102. universal wheel; 103. support column; 104. support frame; 105. side opening; 106. first motor; 107. first rotating shaft; 108. first rotating seat; 2. lifting auxiliary mechanism; 201. fixed frame; 202. first rotating frame; 203. second rotating frame; 204. rotating head; 205. connecting rod; 206. first rotating sleeve; 207. first electric push rod; 208. second rotating sleeve; 209. lap plate; 210. mattress; 211. first pressure sensor; 212. strap; 3. testing mechanism; 301. side baffle; 302. first sliding groove; 303. second motor; 304. first screw rod; 305. first sliding block; 306. range finder; 307. optical fiber refractive index sensor group; 308. air bag; 309. second pressure sensor; 4. detection mechanism; 401. long rod; 402. mounting rod; 403. TOF radar; 404. motion sensor; 405. camera; 406. acousto-optic alarm; 5. headrest mechanism; 501. headstock; 502. second sliding groove; 503. mounting plate; 504. second sliding block; 505. second screw rod; 506. first pulley; 507. transmission belt; 508. second pulley; 509. third motor; 510. second electric push rod; 511. second rotating seat; 512. rotating block; 513. connecting frame; 514. biaxial motor; 515. headrest backrest; and 516. avoidance groove.

DETAILED DESCRIPTION OF THE EMBODIMENTS

In the following, the technical scheme in the embodiment of the disclosure will be clearly and completely described with reference to the attached drawings. Obviously, the described implementation regulations are only part of the embodiment of the disclosure, but not the whole embodiment. Based on the embodiments in the present disclosure, all other embodiments obtained by ordinary technicians in the field without creative labor belong to the scope of protection of the present disclosure.

Embodiment 1: as shown in FIGS. 1-8, the disclosure provides a technical scheme: a monitoring and early warning device for preventing falling during getting up of old people, includes a bedstead mechanism 1, where the top of the bedstead mechanism 1 is provided with a lifting auxiliary mechanism 2, and the top of the bedstead mechanism 1 is symmetrically provided with testing mechanisms 3 near both sides, the back side of the bedstead mechanism 1 is provided with a headrest mechanism 5, and the top of the bedstead mechanism 1 is provided with a detection mechanism 4 near the front side. The lifting auxiliary mechanism 2 includes a fixed frame 201, a first rotating frame 202 and a second rotating frame 203, where tops of the fixed frame 201, the first rotating frame 202 and the second rotating frame 203 are all connected to a plurality of lap plates 209, a mattress 210 is arranged between the tops of the plurality of lap plates 209, first pressure sensors 211 are embedded in the top of the mattress 210, and the two testing mechanisms 3 both include side baffles 301; air bags 308 are installed on the outer surfaces of the opposite sides of the two side baffles 301, and a plurality of second pressure sensors 309 are embedded in the outer surfaces of the opposite sides of the two air bags 308 in an array mode, and optical fiber refractive index sensor groups 307 are symmetrically installed at the positions, close to the inner side, of the tops of the two side baffles 301. The bedstead mechanism 1 includes an underframe 101, where the top of the underframe 101 is fixedly connected to support columns 103 at positions close to four corners; a support frame 104 is fixedly connected between the tops of the plurality of support columns 103, the fixed frame 201 is fixedly connected to the top of the support frame 104 at positions close to the front side, the bottoms of the first rotating frame 202 and the second rotating frame 203 are attached with the top of the support frame 104, two first rotating seats 108 are fixedly connected to a position, close to the rear side, of the top of the underframe 101, and universal wheels 102 are mounted at positions, close to the four corners, of the bottom of the underframe 101. The outer surface of the support frame 104 is provided with side openings 105 at positions close to both sides, and a first rotating shaft 107 is rotatably connected between the front and rear inner surface walls of the side openings 105, the side baffles 301 are located between the inner surface walls of the side openings 105, the outer surface of the first rotating shaft 107 is connected to the inner surface walls of the side baffles 301, and the front surface of the support frame 104 is provided with first motors 106 at positions close to both sides, and output ends of the first motors 106 rotate through the front surface of the support frame 104 and is fixedly connected to the front end of the first rotating shaft 107, the top of the side baffle 301 is provided with a first sliding groove 302 near the outside, a first screw rod 304 is rotatably connected between the front and rear inner surface walls of the first sliding groove 302, a first sliding block 305 is slidably embedded between the inner surface walls of the first sliding groove 302, and the outer surface of the first screw rod 304 is threaded through the outer surface of the first sliding block 305, the front surface of the side baffle 301 is provided with a second motor 303, the output end of the second motor 303 rotates through the front surface of the side baffle 301 and extends to the other side, the output end of the second motor 303 is fixedly connected to the front end of the first screw rod 304, the top of the first sliding block 305 is provided with a range finder 306. The detection mechanism 4 includes a long rod 401, the long rod 401 is fixedly installed at the top of the support frame 104 near the front side, the top of the long rod 401 is fixedly connected to a mounting rod 402, a camera 405 is arranged at the bottom of the mounting rod 402 near the rear edge; a motion sensor 404 is arranged at the front side of the camera 405 at the bottom of the mounting rod 402; a TOF radar 403 is arranged at the front side of the motion sensor 404 at the bottom of the mounting rod 402; and an acousto-optic alarm 406 is arranged at the top of the mounting rod 402.

In this embodiment, when in use, the optical fiber refractive index sensor groups 307 on the two sides form a detection horizontal line, the horizontal height of the detection line is consistent with the height of the side baffles 301, and is slightly higher than the old people in the sleep state; meanwhile, the airbags 308 on both sides prevent the old people from bumping, and a large number of sensor matrix consisting of second pressure sensors 309 are installed inside. In addition, under the mutual cooperation of a sensor matrix consisting of a large number of first pressure sensors 211 in the mattress 210, the position of the old people in the rest on the mattress 210 can be detected according to the pressure values and the pressure distribution. When the pressure distribution area decreases and the optical fiber refractive index sensor groups 307 detects the electrical signal, the getting-up action of the old people can be judged. At this time, the second motor 303 is started at the same time to drive the first screw rod 304 to rotate according to the pressure concentration position of the first pressure sensors 211, and after the first lead screw 304 rotates, the first sliding blocks 305 are driven to move front and back. At this time, the first sliding blocks 305 on both sides drive the range finder 306 to move to the left and right positions of the sitting old people according to the feedback signal of the first pressure sensors 211. At the moment, the range finder 306 on the two sides detect the distance of the old people, after the distance is close, the old people are judged to start the getting-up action. When the old people are close, the corresponding first motor 106 starts synchronously and drives the first rotating shaft 107 to rotate outwards, and then drives the corresponding side baffle 301 to turn outwards by 180 degrees and then fold down, thus facilitating the old people to get out of bed, and when the first pressure sensors 211 and the second pressure sensors 309 receive a continuous electric signal, the motion sensor 404 and the TOF radar 403 in the detection mechanism 4 can be started. In the whole process of the old people getting out of the bed, the motion sensor 404 continuously monitors the motion speed of the old people, and the TOF radar 403 monitors the external area of the device. When the motion sensor 404 monitors a instantaneous acceleration behavior, it is judged that the old people fall, and when the TOF radar 403 detects a long-term static behavior of the old people in the external area of the device, it is judged that the old people drop. Abnormal behavior activates the acousto-optic alarm and sends early warnings to the intelligent terminals of accompanying personnel and medical staff through a built-in module for warning. Staff unable to offer immediate help could turn on the camera 405 to watch the image information near the device through the intelligent terminal at this time, and take actions based on the old people's condition. The disclosure has high overall intelligence, can effectively avoid falling accidents caused by the old people getting up alone, and has a good guarding effect.

During the whole use process, after the side baffle 301 is driven to the upward vertical state by the first motors 106 and the first rotating shaft 107, the old people on the bed can be prevented from falling from the side face, the support columns 103 in the device are mainly used for connecting the underframe 101 and the support frame 104, the universal wheels 102 play a role in conveniently moving the device, the length of the long rod 401 is 2 m, and the matched mounting rod 402 is mainly used for installing the TOF radar 403, the motion sensor 404, the camera 405 and the acousto-optic alarm 406.

Figure 2:
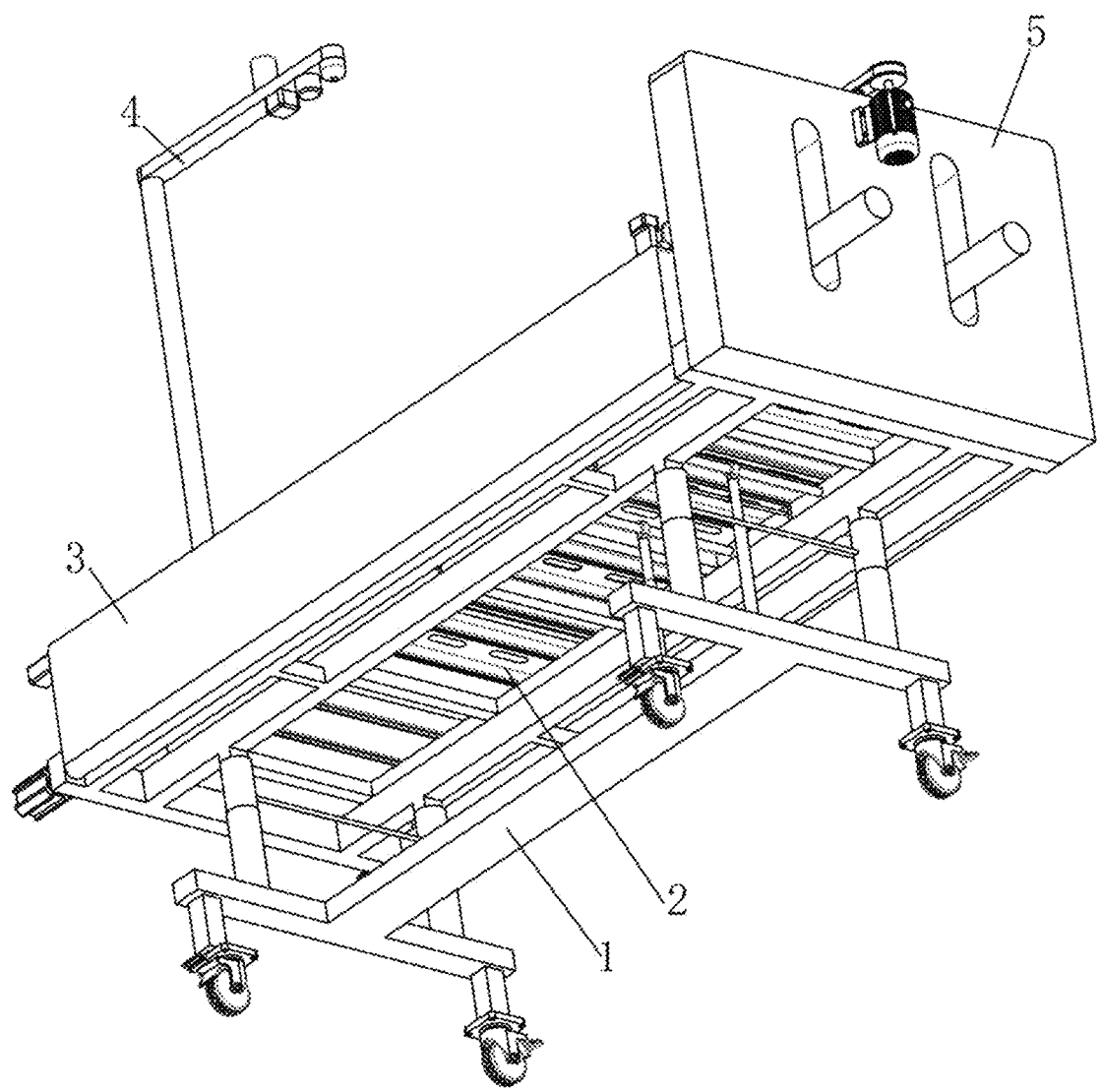
FIG. 2 is another perspective view of the monitoring and early warning device for preventing falling during getting up of old people.
Figure 3:
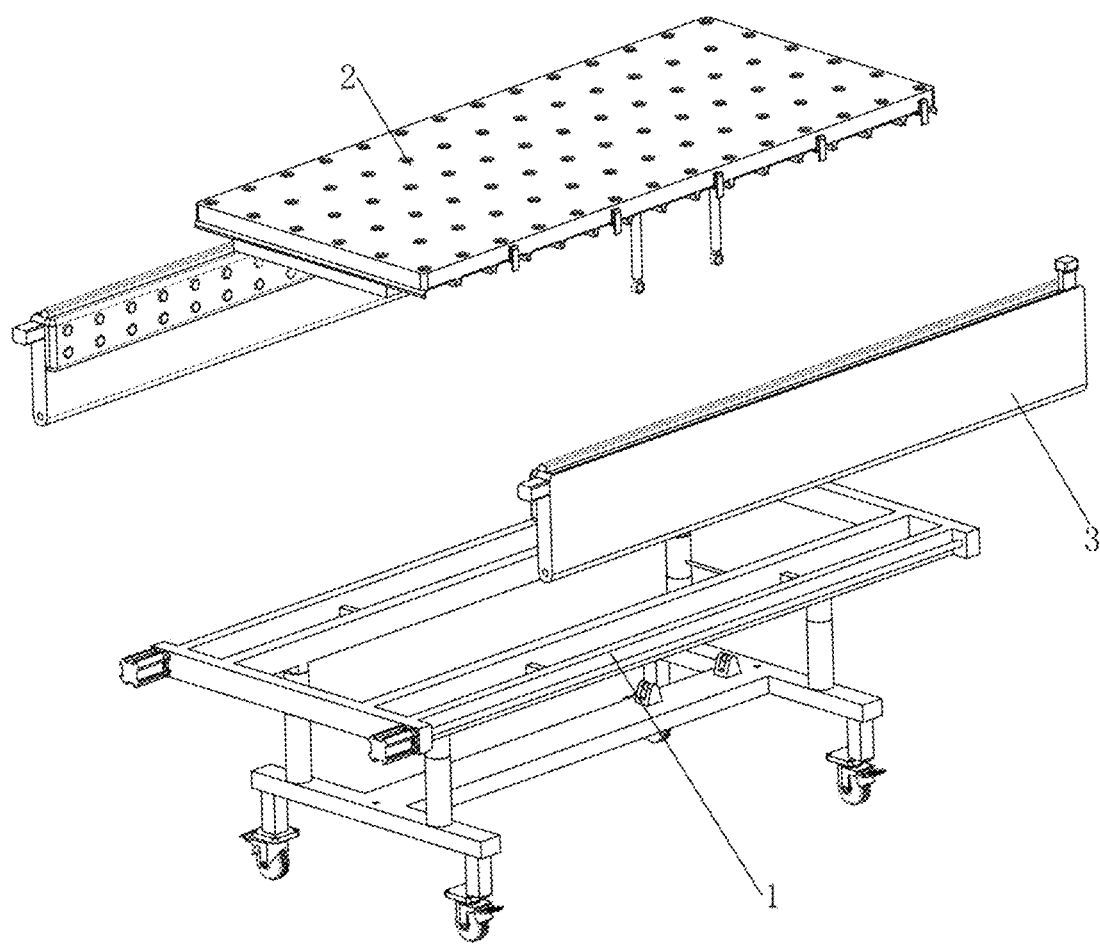
FIG. 3 is a partial structure expansion diagram of the monitoring and early warning device for preventing falling during getting up of old people.
Figure 4:
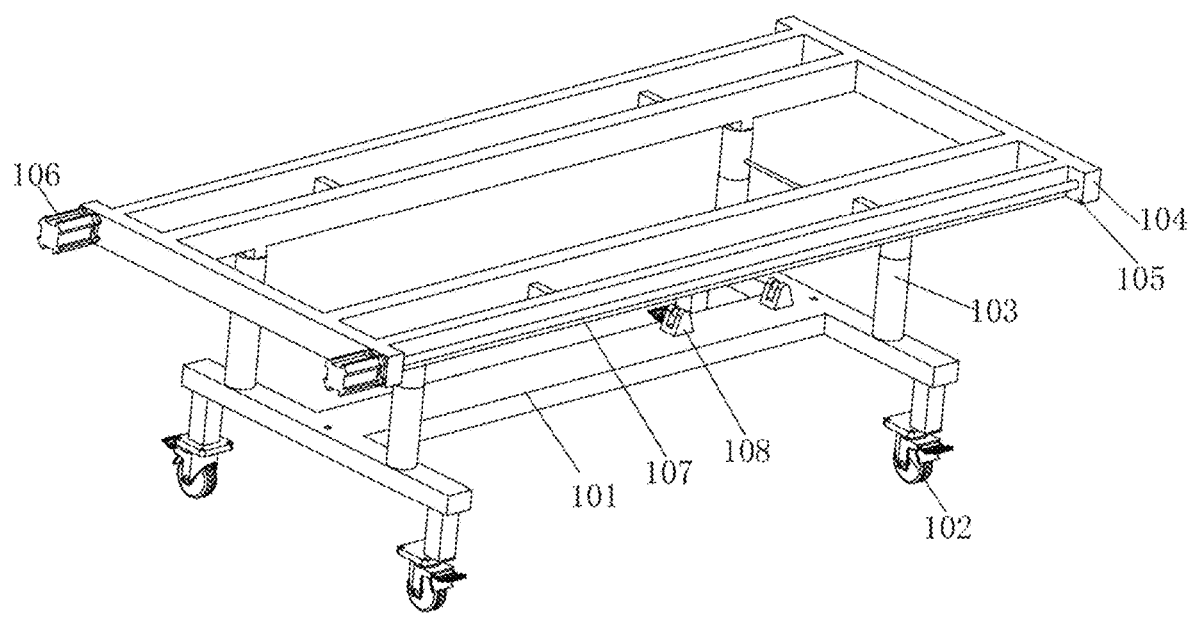
FIG. 4 is a schematic structural diagram of a bedstead mechanism of the monitoring and early warning device for preventing falling during getting up of old people.
Figure 5:
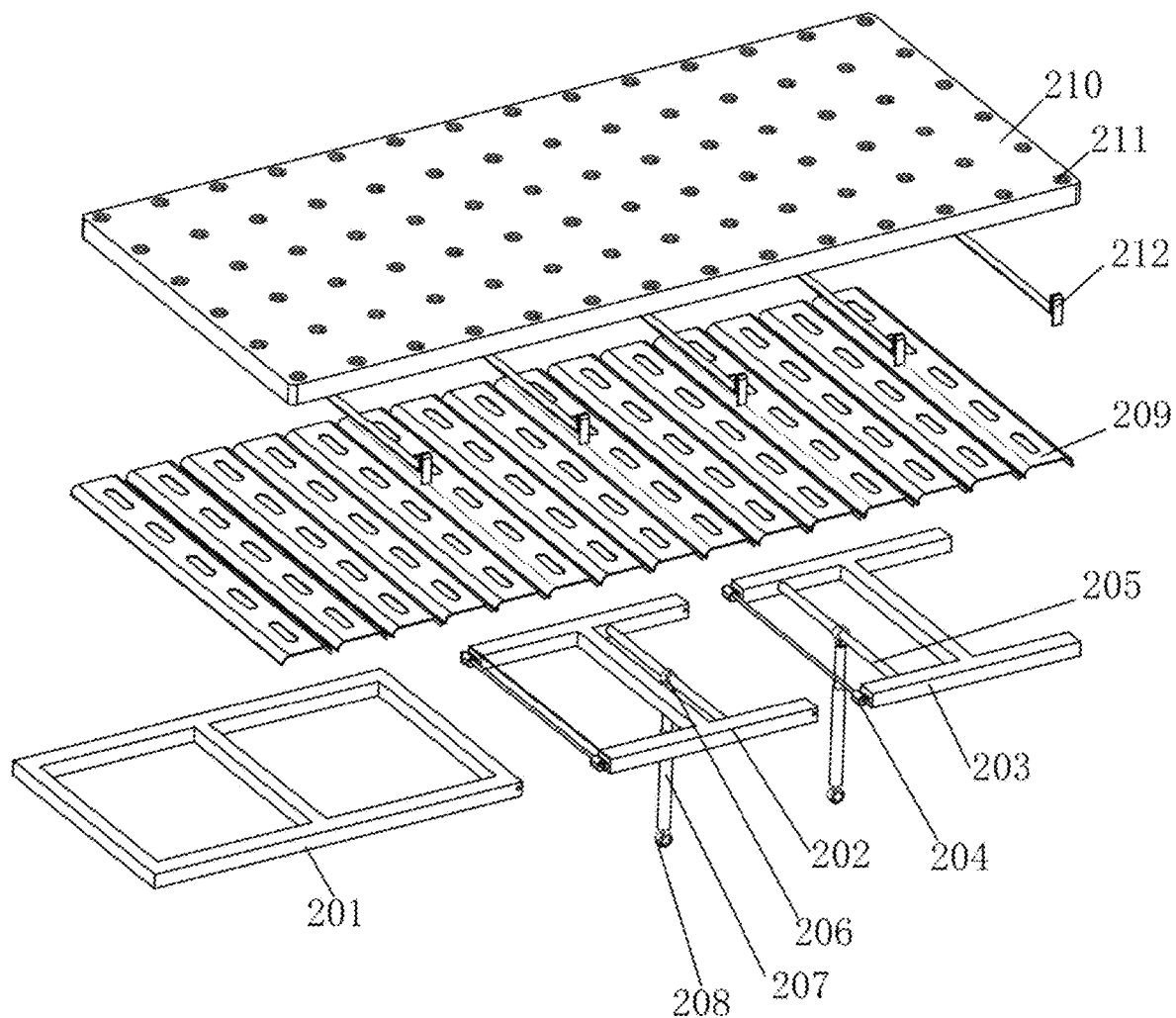
FIG. 5 is a schematic structural diagram of a lifting auxiliary mechanism of the monitoring and early warning device for preventing falling during getting up of old people.
Figure 6:
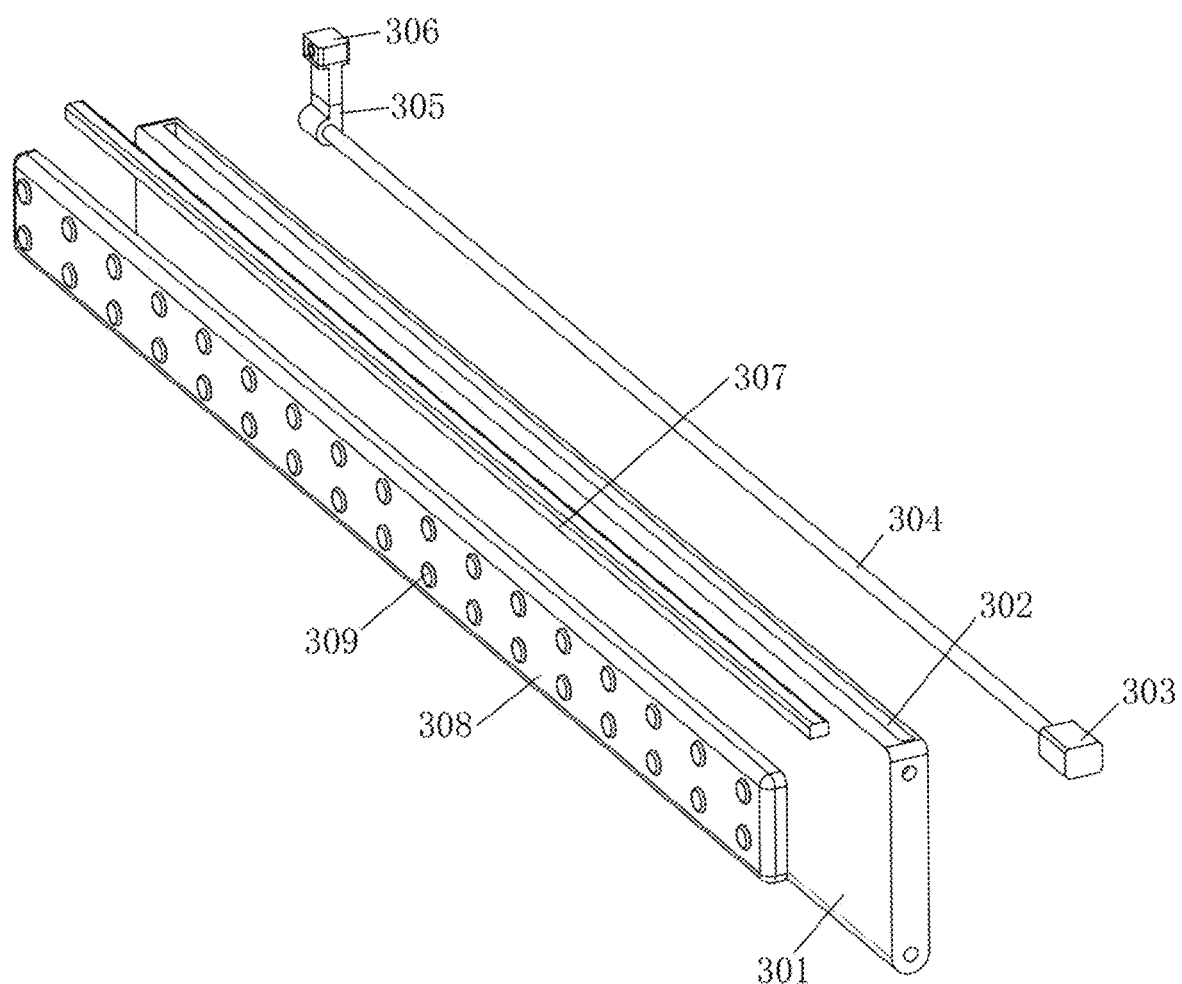
FIG. 6 is a schematic structural diagram of a testing mechanism of the monitoring and early warning device for preventing falling during getting up of old people.
Figure 7:
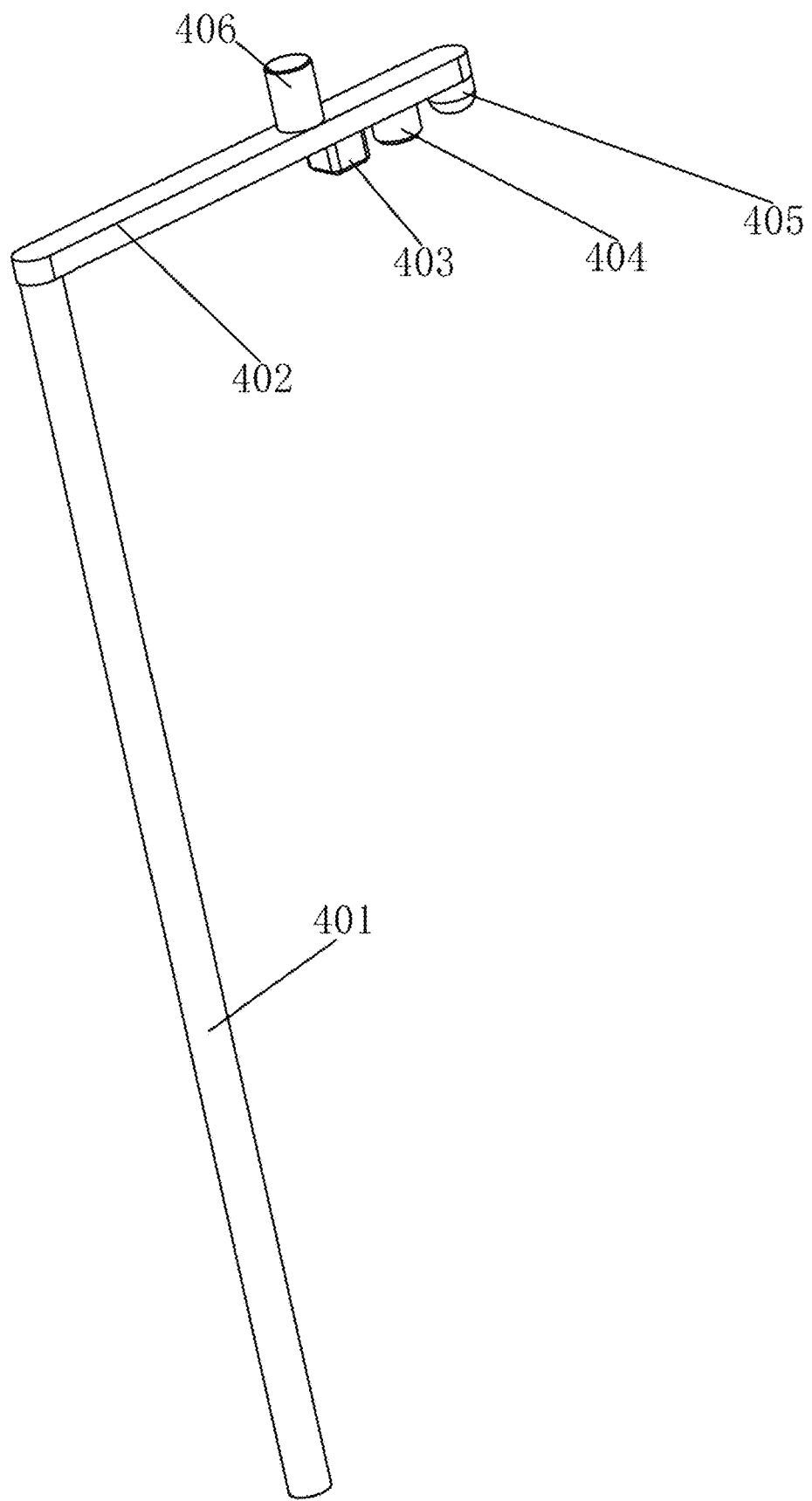
FIG. 7 is a schematic structural diagram of a detection mechanism of the monitoring and early warning device for preventing falling during getting up of old people.

Embodiment 2: as shown in FIG. 2, FIG. 3 and FIG. 5, rotating heads 204 are installed on the front surfaces of the first rotating frame 202 and the second rotating frame 203, where one rotating head 204 is rotatably connected to the rear surface of the fixed frame 201, and the other rotating head 204 is rotatably connected to the rear surface of the first rotating frame 202, and connecting rods 205 are fixedly connected between the inner surface walls of both sides of the first rotating frame 202 and the second rotating frame 203. The outer surface of the connecting rod 205 is rotatably connected to a first rotating sleeve 206, the bottom of the first rotating sleeve 206 is connected to a first electric push rod 207, the bottom of the first electric push rod 207 is connected to a second rotating sleeve 208, and the two second rotating sleeves 208 are rotatably connected to the two first rotating seats 108 respectively. The outer surface of the mattress 210 is provided with a strap 212, and the outer surface of the strap 212 passes through the bottom of the adjacent lap plates 209.

In this embodiment, the lap plate 209 is integrally U-shaped, an arc-shaped angle is formed in the top edge of the lap plate 209 to prevent the mattress 210 from being scratched, a space for inserting the strap 212 is reserved at the bottom of the lap plate 209, and after the two ends of the strap 212 and the mattress 210 are fixed, the mattress 210 can be effectively prevented from sliding. The rear sides of the fixed frame 201 and the first rotating frame 202 are both provided with L-shaped inner grooves, and the rotating head 204 is L-shaped with a shaft rotatably connected inside, the shaft is rotatably connected with the L-shaped inner groove, so that the first rotating frame 202 and the second rotating frame 203 can both rotate upwards. When the first pressure sensors 211 and the second pressure sensors 309 detect the old people getting up, the first pressure sensors 211 judge the position where the upper body of the old people is propped up according to the area where the pressure is weakened, and the first electric push rod 207 at the corresponding position according to the position where the old people get up simultaneously starts to extend and push the connecting rod 205 to move upwards. At this time, the corresponding first rotating frame 202 and second rotating frame 203 are reversed upwards, so as to push the upper body of the old people to form a booster, and the corresponding part of the mattress 210 is lifted. Meanwhile, the lifted first pressure sensors 211 feed back the pressure value to the first electric push rod 207 for controlling the pushing speed. The device, with high level of intelligence and ease of use, facilitates the old people in getting up independently, making the process more convenient with mutual coordination. During the expansion and contraction of the first electric push rod 207, the first rotating sleeve 206 at the top rotates with the connecting rod 205, and the second rotating sleeve 208 at the bottom rotates with the first rotating seats 108 on the underframe 101, thus eliminating motion interference.

Figure 8:
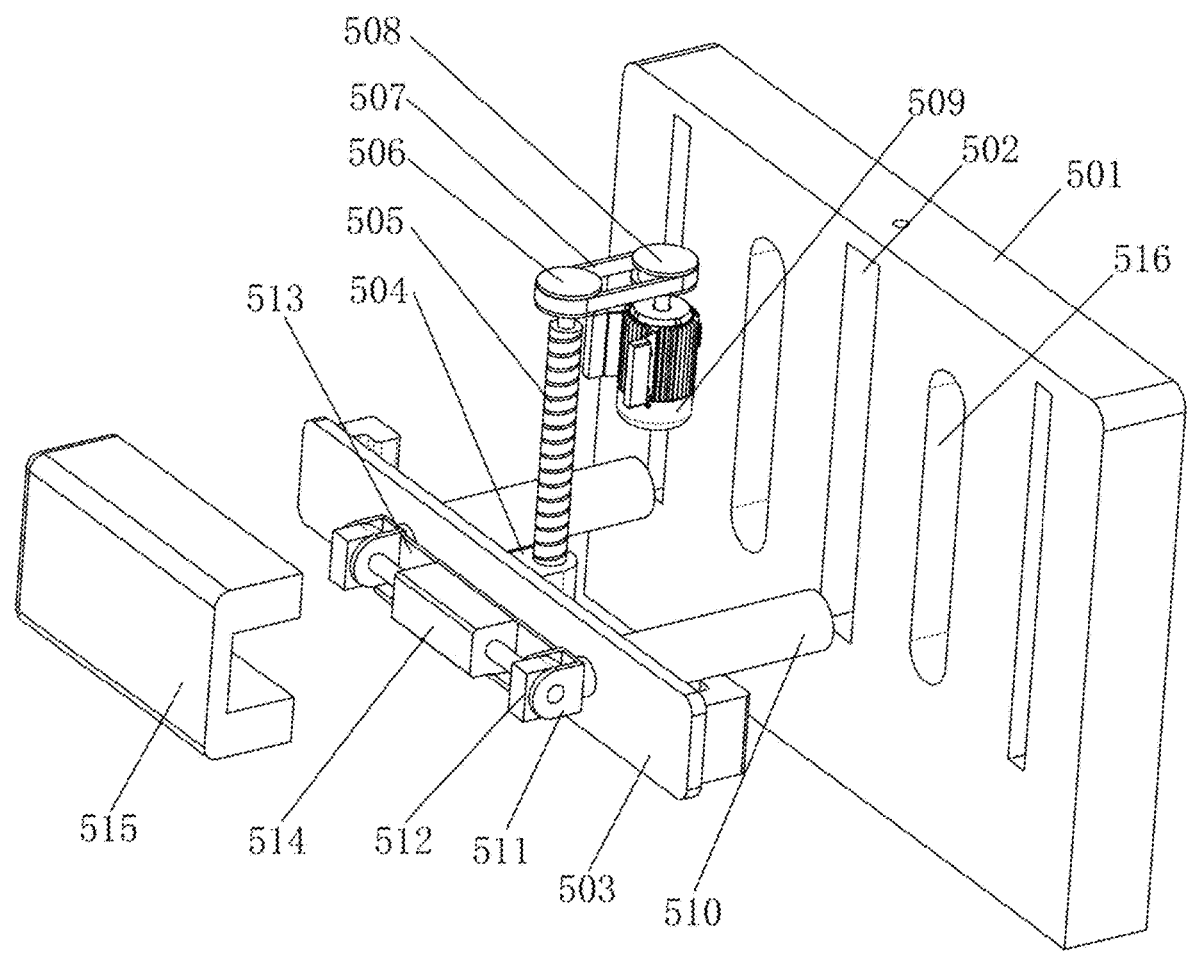
FIG. 8 is a schematic structural diagram of a headrest mechanism of the monitoring and early warning device for preventing falling during getting up of old people.

Embodiment 3: as shown in FIG. 1, FIG. 2 and FIG. 8, the headrest mechanism 5 includes a headstock 501. The front surface of the headstock 501 near the bottom is fixedly connected to the rear surface of the support frame 104. The front surface of the headstock 501 is slidably connected to a mounting plate 503, and a second sliding groove 502 is formed in the front surface of the headstock 501 near the middle. A second screw rod 505 is rotatably connected between the inner top and the inner bottom of the second sliding groove 502, and a second sliding block 504 is fixedly connected to the rear surface of the mounting plate 503 near the middle, the outer surface of the second screw rod 505 is threaded through the outer surface of the second sliding block 504, the top center of the headstock 501 is rotatably connected to a first pulley 506, the bottom of the first pulley 506 is fixedly connected to the top of the second screw rod 505 through a shaft, a third motor 509 is fixedly installed on the rear surface of the headstock 501; the output end of the third motor 509 is fixedly connected to a second pulley 508, and a transmission belt 507 is connected between the second pulley 508 and the outer surface of the first pulley 506 in a transmission way; the front surface of the headstock 501 is symmetrically provided with avoidance grooves 516 at positions on both sides of the second sliding groove 502, and second electric push rods 510 are symmetrically mounted on the rear surface of the mounting plate 503. The telescopic ends of the second electric push rods 510 slide through the rear surface of the mounting plate 503 and extend to the front side, the second electric push rods 510 are located between the inner surface walls of the avoidance grooves 516, the front ends of the two second electric push rods 510 are fixedly connected to second rotating seats 511, and rotating blocks 512 are rotatably connected between the inner surface walls of the second rotating seats 511; a headrest backrest 515 is fixedly connected between the front surfaces of the two rotating blocks 512. A connecting frame 513 is fixedly connected between the outer surfaces of the two second rotating seats 511, and a biaxial motor 514 is installed on the front surface of the connecting frame 513. The output ends at both sides of the biaxial motor 514 respectively penetrate the outer surfaces of the two second rotating seats 511 and are connected to the two rotating blocks 512.

In this embodiment, during use, the third motor 509 is started to drive the second pulley 508 to rotate according to the sleep or sitting state of the old people, the first pulley 506 is synchronously driven to rotate through cooperation of the transmission belt 507. When the first pulley 506 rotates, the second screw rod 505 in the second sliding groove 502 is driven to rotate, a second sliding block 504 is driven to ascend and descend. In the lifting process of the second sliding block 504, the headrest backrest 515 is driven by the mounting plate 503 and other mechanisms to be adjusted to a low position, so that old people can use the headrest backrest 515 as a pillow or be adjusted to a high position to serve as a backrest, while in the getting-up process of old people, the headrest backrest 515 is adjusted to a medium height, after the second electric push rod 510 is started, the headrest backrest 515 is pushed to be attached to the back of the old people and slowly pushed forwards for providing assisting force. In the process, the biaxial motor 514 drives the rotating blocks 512 in the two second rotating seats 511 to overturn up and down to adjust the angle of the headrest backrest 515, so that the headrest backrest 515 is always attached to the back of the old people, the comfort degree in the pushing process is improved, the effect of assisting the old people in sitting is achieved, the practicability of the device is improved. The avoidance groove 516 is mainly used to avoid the main body of the lifting second electric push rod 510, and the connecting frame 513 is mainly used to install the biaxial motor 514.

The effect and working principle of the whole mechanism are as follows: when in use, the optical fiber refractive index sensor groups 307 on the two sides form a detection horizontal line, the horizontal height of the detection line is consistent with the height of the side baffles 301, and is slightly higher than the old people in the sleep state; meanwhile, the airbags 308 on both sides prevent the old people from bumping, and a large number of sensor matrix consisting of second pressure sensors 309 are installed inside. In addition, under the mutual cooperation of a sensor matrix consisting of a large number of first pressure sensors 211 in the mattress 210, the position of the old people in the rest on the mattress 210 can be detected according to the pressure values and the pressure distribution. When the pressure distribution area decreases and the optical fiber refractive index sensor groups 307 detects the electrical signal, the getting-up action of the old people can be judged. At this time, the second motor 303 is started at the same time to drive the first screw rod 304 to rotate according to the pressure concentration position of the first pressure sensors 211, and after the first lead screw 304 rotates, the first sliding blocks 305 are driven to move front and back. At this time, the first sliding blocks 305 on both sides drive the range finder 306 to move to the left and right positions of the sitting old people according to the feedback signal of the first pressure sensors 211. At the moment, the range finder 306 on the two sides detect the distance of the old people, after the distance is close, the old people are judged to start the getting-up action. When the old people are close, the corresponding first motor 106 starts synchronously and drives the first rotating shaft 107 to rotate outwards, and then drives the corresponding side baffle 301 to turn outwards by 180 degrees and then fold down, thus facilitating the old people to get out of bed, and when the first pressure sensors 211 and the second pressure sensors 309 receive a continuous electric signal, the motion sensor 404 and the TOF radar 403 in the detection mechanism 4 can be started. In the whole process of the old people getting out of the bed, the motion sensor 404 continuously monitors the motion speed of the old people, and the TOF radar 403 monitors the external area of the device. When the motion sensor 404 monitors a instantaneous acceleration behavior, it is judged that the old people fall, and when the TOF radar 403 detects a long-term static behavior of the old people in the external area of the device, it is judged that the old people drop. Abnormal behavior activates the acousto-optic alarm and sends early warnings to the intelligent terminals of accompanying personnel and medical staff through a built-in module for warning. Staff unable to offer immediate help could turn on the camera 405 to watch the image information near the device through the intelligent terminal at this time, and take actions based on the old people's condition. The disclosure has high overall intelligence, can effectively avoid falling accidents caused by the old people getting up alone, and has a good guarding effect. In addition, When the first pressure sensors 211 and the second pressure sensors 309 detect the old people getting up, the first pressure sensors 211 judge the position where the upper body of the old people is propped up according to the area where the pressure is weakened, and the first electric push rod 207 at the corresponding position according to the position where the old people get up simultaneously starts to extend and push the connecting rod 205 to move upwards. At this time, the corresponding first rotating frame 202 and second rotating frame 203 are reversed upwards, so as to push the upper body of the old people to form a booster, and the corresponding part of the mattress 210 is lifted. Meanwhile, the lifted first pressure sensors 211 feed back the pressure value to the first electric push rod 207 for controlling the pushing speed. The device, with high level of intelligence and ease of use, facilitates the old people in getting up independently, making the process more convenient with mutual coordination, the third motor 509 is started to drive the second pulley 508 to rotate according to the sleep or sitting state of the old people, the first pulley 506 is synchronously driven to rotate through cooperation of the transmission belt 507. When the first pulley 506 rotates, the second screw rod 505 in the second sliding groove 502 is driven to rotate, a second sliding block 504 is driven to ascend and descend. In the lifting process of the second sliding block 504, the headrest backrest 515 is driven by the mounting plate 503 and other mechanisms to be adjusted to a low position, so that old people can use the headrest backrest 515 as a pillow or be adjusted to a high position to serve as a backrest, while in the getting-up process of old people, the headrest backrest 515 is adjusted to a medium height, after the second electric push rod 510 is started, the headrest backrest 515 is pushed to be attached to the back of the old people and slowly pushed forwards for providing assisting force. In the process, the biaxial motor 514 drives the rotating blocks 512 in the two second rotating seats 511 to overturn up and down to adjust the angle of the headrest backrest 515, so that the headrest backrest 515 is always attached to the back of the old people, the comfort degree in the pushing process is improved, the effect of assisting the old people in sitting is achieved, the practicability of the device is improved.

Although the present disclosure has been described in detail with reference to the foregoing embodiments, it is still possible for a person skilled in the art to modify the technical scheme described in the foregoing embodiments or to replace some technical features by equivalents. Any modification, equivalent replacement, improvement, etc. made within the spirit and principle of the present disclosure should be included in the protection scope of the present disclosure.

What is claimed is:

1. A monitoring and early warning device for preventing falling during getting up of old people, comprising a bedstead mechanism (1), wherein a top of the bedstead mechanism (1) is provided with a lifting auxiliary mechanism (2), and the top of the bedstead mechanism (1) is symmetrically provided with testing mechanisms (3) near both sides of the bedstead mechanism (1), a back side of the bedstead mechanism (1) is provided with a headrest mechanism (5), and the top of the bedstead mechanism (1) is provided with a detection mechanism (4) near a front side of the bedstead mechanism (1);

the lifting auxiliary mechanism (2) comprises a fixed frame (201), a first rotating frame (202) and a second rotating frame (203), wherein tops of the fixed frame (201), the first rotating frame (202) and the second rotating frame (203) are all connected to a plurality of lap plates (209), a mattress (210) is arranged between tops of the plurality of lap plates (209), first pressure sensors (211) are embedded in a top of the mattress (210);

the two testing mechanisms (3) both comprise side baffles (301); air bags (308) are installed on outer surfaces of opposite sides of the two side baffles (301), and a plurality of second pressure sensors (309) are embedded in outer surfaces of opposite sides of the two air bags (308) in an array mode, and optical fiber refractive index sensor groups (307) are symmetrically installed at positions, close to an inner side, of tops of the two side baffles (301);

the bedstead mechanism (1) comprises an underframe (101), wherein a top of the underframe (101) is fixedly connected to support columns (103) at positions close to four corners; a support frame (104) is fixedly connected between tops of the support columns (103), the fixed frame (201) is fixedly connected to a top of the support frame (104) at positions close to a front side of the support frame (104), bottoms of the first rotating frame (202) and the second rotating frame (203) are attached with the top of the support frame (104), two first rotating seats (108) are fixedly connected to a position, close to a rear side, of the top of the underframe (101), and universal wheels (102) are mounted at positions, close to four corners, of a bottom of the underframe (101);

an outer surface of the support frame (104) is provided with side openings (105) at positions close to both sides, and a first rotating shaft (107) is rotatably connected between front and rear inner surface walls of the side openings (105), the side baffles (301) are located between inner surface walls of the side openings (105), an outer surface of the first rotating shaft (107) is connected to inner surface walls of the side baffles (301), and a front surface of the support frame (104) is provided with first motors (106) at positions close to both sides, and output ends of the first motors (106) rotate through the front surface of the support frame (104) and is fixedly connected to a front end of the first rotating shaft (107);

the top of the side baffle (301) is provided with a first sliding groove (302) near an outside of the side baffle (301), a first screw rod (304) is rotatably connected between front and rear inner surface walls of the first sliding groove (302), a first sliding block (305) is slidably embedded between inner surface walls of the first sliding groove (302), and an outer surface of the first screw rod (304) is threaded through an outer surface of the first sliding block (305);

a front surface of the side baffle (301) is provided with a second motor (303), an output end of the second motor (303) rotates through the front surface of the side baffle (301) and extends to a side of the side baffle (301), the output end of the second motor (303) is fixedly connected to a front end of the first screw rod (304), a top of the first sliding block (305) is provided with a range finder (306); and the detection mechanism (4) comprises a rod (401), the rod (401) is fixedly installed at the top of the support frame (104) near the front side of the support frame (104), a top of the rod (401) is fixedly connected to a mounting rod (402), a camera (405) is arranged at a bottom of the mounting rod (402) near a rear edge of the mounting rod (402); a motion sensor (404) is arranged at a front side of the camera (405) at the bottom of the mounting rod (402); a time of flight (TOF) radar (403) is arranged at a front side of the motion sensor (404) at the bottom of the mounting rod (402); and an acousto-optic alarm (406) is arranged at a top of the mounting rod (402).

2. The monitoring and early warning device for preventing falling during getting up of old people according to claim 1, wherein rotating heads (204) are installed on front surfaces of the first rotating frame (202) and the second rotating frame (203), one rotating head (204) is rotatably connected to a rear surface of the fixed frame (201), another rotating head (204) is rotatably connected to a rear surface of the first rotating frame (202), and connecting rods (205) are fixedly connected between inner surface walls of both sides of the first rotating frame (202) and the second rotating frame (203).

3. The monitoring and early warning device for preventing falling during getting up of old people according to claim 2, wherein an outer surface of the connecting rod (205) is rotatably connected to a first rotating sleeve (206), a bottom of the first rotating sleeve (206) is connected to a first electric push rod (207), a bottom of the first electric push rod (207) is connected to a second rotating sleeve (208), and the two second rotating sleeves (208) are rotatably connected to the two first rotating seats (108) respectively; an outer surface of the mattress (210) is provided with a strap (212), and an outer surface of the strap (212) passes through a bottom of the adjacent lap plates (209).

4. The monitoring and early warning device for preventing falling during getting up of old people according to claim 3, wherein the headrest mechanism (5) comprises a headstock (501); a front surface of the headstock (501) near a bottom of the headstock (501) is fixedly connected to a rear surface of the support frame (104); the front surface of the headstock (501) is slidably connected to a mounting plate (503), and a second sliding groove (502) is formed in the front surface of the headstock (501) near a middle of the headstock (501); a second screw rod (505) is rotatably connected between an inner top and an inner bottom of the second sliding groove (502), and a second sliding block (504) is fixedly connected to a rear surface of the mounting plate (503) near a middle of the mounting plate (503), an outer surface of the second screw rod (505) is threaded through an outer surface of the second sliding block (504), a top center of the headstock (501) is rotatably connected to a first pulley (506), a bottom of the first pulley (506) is fixedly connected to a top of the second screw rod (505)

through a shaft, a third motor (509) is fixedly installed on a rear surface of the headstock (501); an output end of the third motor (509) is fixedly connected to a second pulley (508), and a transmission belt (507) is connected between the second pulley (508) and an outer surface of the first pulley (506) in a transmission way.

5. The monitoring and early warning device for preventing falling during getting up of old people according to claim 4, wherein the front surface of the headstock (501) is symmetrically provided with avoidance grooves (516) at positions on both sides of the second sliding groove (502), and second electric push rods (510) are symmetrically mounted on the rear surface of the mounting plate (503); telescopic ends of the second electric push rods (510) slide through the rear surface of the mounting plate (503) and extend to a front side thereof, the second electric push rods (510) are located between inner surface walls of the avoidance grooves (516), front ends of the two second electric push rods (510) are fixedly connected to second rotating seats (511), and rotating blocks (512) are rotatably connected between inner surface walls of the second rotating seats (511); a headrest backrest (515) is fixedly connected between front surfaces of the two rotating blocks (512); a connecting frame (513) is fixedly connected between outer surfaces of the two second rotating seats (511), and a biaxial motor (514) is installed on a front surface of the connecting frame (513); output ends at both sides of the biaxial motor (514) respectively penetrate outer surfaces of the two second rotating seats (511) and are connected to the two rotating blocks (512).

* * * * *